United States Patent [19]
Babler et al.

[11] Patent Number: 6,049,010
[45] Date of Patent: Apr. 11, 2000

[54] METHOD OF PREPARING 3-(3-METHYL-2-BUTEN-1-YL)-2,4-PENTANEDIONE AND RELATED DICARBONYL COMPOUNDS

[75] Inventors: James H. Babler, Chicago, Ill.; Harvey W. Posvic, Carey Township, Wis.

[73] Assignee: Loyola University of Chicago, Chicago, Ill.

[21] Appl. No.: 09/161,983

[22] Filed: Sep. 29, 1998

[51] Int. Cl.$^7$ .................................................. C07C 45/45
[52] U.S. Cl. ...................... 568/395; 568/383; 568/388; 560/178; 560/203; 560/205
[58] Field of Search .................... 568/382, 383, 568/388, 395, 417; 560/178, 203, 205

[56] References Cited

U.S. PATENT DOCUMENTS

| | | | |
|---|---|---|---|
| 5,349,071 | 9/1994 | Babler | 549/423 |
| 5,569,778 | 10/1996 | Umemoto et al. | 560/121 |

OTHER PUBLICATIONS

House, Modern Synthetic Reactions, Second Edition, pp. 492–493, 1972.
Chemical Abstracts, 48, 710a (1954) of British patent 681, 196 (Oct. 22, 1952).
Chemical Abstracts, 51, 7313a (1957) of Y.R. Naves, et al., Bull. Soc. Chim. Fr., 1409 (1956).
Chemical Abstracts, 51, 12143h (1957) of British patent 762,656 (Dec. 5, 1956).
Chemical Abstracts, 52, 9961f (1958) of K.K. Georgieff, Ind. Eng. Chem., 49, 1067 (1957).
Chemical Abstracts, 52, 19950f (1958) of U.S. Patent No. 2,834,811 (May 13, 1958).
Chemical Abstracts, 59, 431c (1963) of A. A. Petrov, et al., Zh. Obshch. Khim. (1963), 33, 427.
Chemical Abstracts, 62, 13049e (1965) of Czech. Patent 112,243 (Oct. 15, 1964).
Chemical Abstracts, 69, 86376m (1968) of German patent 1,268,135 (May 16, 1968).
Chemical Abstracts, 70, 37941d (1969) of Czech. Patent 126,763 (Mar. 15, 1968).
Chemical Abstracts, 70, 67626x (1969) of U.S. Patent No. 3,420,827 (Jan. 7, 1969).
Chemical Abstracts, 73, 120090h (1970) of German patent 1,914,376 (Oct. 1, 1970).
Chemical Abstracts, 86, 89179m (1977) of U.S. Patent No. 3,998,872 (Dec. 21, 1976).
Chemical Abstracts, 93, 26559j (1980).
Chemical Abstracts, 96, 199115b (1982) of European Patent Appl. EP 44,771 (Jan. 27, 1982).
Chemical Abstracts, 105, 171857a (1986) of French patent 2,567,511 (Jan. 17, 1986).
Organic Syntheses, Collective vol. 5, 767–769 (1973).
Organic Synthesis, vol. 30, 18–21 (1950).
Boatman, et al., "Synthesis of Ketones of the Type $CH_3COCH_2R$," 30, 3321–3324, (1965).
H. Hibbert, et al., J. Am. Chem. Soc., 46, 119–130, (1924).
S. Julia, et al., Bull. Soc. Chim. France, 3490–3498, (1966).
Kimel, et al., The Journal of Organic Chemistry, 23, 153–157, (1958).
J. Marquet, et al., Synthesis, 348–350, (1979).
J. Marquet, et al., Tetrahedron Lett., 29, 1465–1468, (1988).
J. A. Miller, et al., J.Chem.Soc. Perkin I, 692–699, (1972).
M. Moreno–Manas, et al., Tetrahedron, 37, 3009–3015, (1981).
H. Pommer, et al., Justus Liebigs Ann. Chem., 52–63, (1969).
Reif, et al., Chemie–Ing.–Tech., 646–652, (1973).
G. Saucy, et al. Helv. Chim. Acta, 50, 1158–1167, (1967).
H.H. Szmant, "Organic Building Blocks of the Chemical Industry," Wiley–Interscience: New York, p. 317, (1989).
"The Merck Index," Ninth Edition, 956, (1976).
Organic Syntheses, Collective Vol. 3, 747–750 (1955).
Morrison et al., Organic Chemistry, Third Edition, 600 (1973).

Primary Examiner—Gary Geist
Assistant Examiner—Sreeni Padmanabhan
Attorney, Agent, or Firm—Marshall, O'Toole, Gerstein, Murray & Borun

[57] ABSTRACT

A method for preparation of a dicarbonyl compound of the following formula

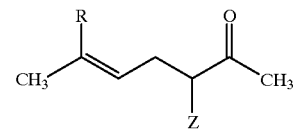

by reacting a conjugated alkadiene compound of the formula

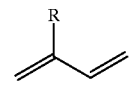

with a 1,3-dicarbonyl compound of the formula

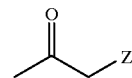

in the presence of an acid catalyst. The products of the method are useful in the preparation of compounds such as vitamins A and E, various carotenoids, Retin A, dehydrolinalool, pseudoionone, citral, and linalool.

21 Claims, No Drawings

METHOD OF PREPARING 3-(3-METHYL-2-BUTEN-1-YL)-2,4-PENTANEDIONE AND RELATED DICARBONYL COMPOUNDS

BACKGROUND OF THE INVENTION

1. Field of the Invention

The present invention describes a method for preparing dicarbonyl compounds of the general formula:

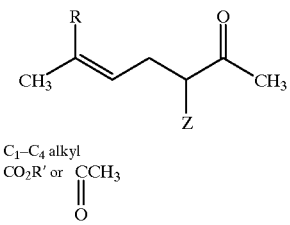
(7)

wherein R = $C_1$–$C_4$ alkyl
Z = $CO_2R'$ or $CCH_3$ with =O
and R' = $C_1$–$C_4$ alkyl.

In one embodiment, "R" is $CH_3$ and "Z" is $COCH_3$, and a product known as 3-(3-methyl-2-buten-1-yl)-2,4-pentanedione is formed, shown in the following formula:

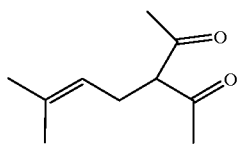
(7a)

In another embodiment, "R" is $CH_3$ and "Z" is $CO_2CH_2CH_3$, and the product, ethyl 2-(3-methyl-2-buten-1-yl)-3-oxobutanoate, is formed, shown in the following formula:

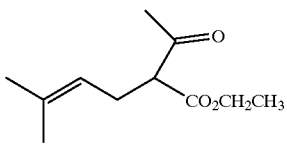
(7b)

2. Description of Related Art (a) Prior Art Processes for Preparation of Dicarbonyl Compounds (7)

The invention relates to a new method for conversion of isoprene (or other 2-alkyl-1,3-butadienes) to dicarbonyl compounds of the general structure (7). For previous syntheses of 3-(3-methyl-2-buten-1-yl)-2,4-pentanedione (7a), see the following:

(a) European Patent Appl. EP 44,771 (Jan. 27, 1982) [*Chem. Abstracts* 1982, 96, 199115b].

(b) J. A. Miller, et al., *J. Chem. Soc. Perkin I* 1972, 692.

(c) H. Pommer, et al., *Justus Liebigs Ann. Chem.* 1969, 729, 52.

(d) German patent 1,914,376 (Oct. 1, 1970) [*Chem. Abstracts* 1970, 73, 120090h].

(e) U.S. Pat. No. 3,998,872 (Dec. 21, 1976) [*Chem. Abstracts* 1977, 86, 89179m].

(f) J. Marquet and M. Moreno-Manas, *Synthesis* 1979, 348.

(g) *Chem. Abstracts* 1980, 93, 26559j.

(h) M. Moreno-Manas and A. Trius, *Tetrahedron* 1981, 37, 3009.

(i) J. Marquet, et al., *Tetrahedron Lett.* 1988, 29, 1465.

All of the above routes involved multi-step processes and/or costly reagents; and all involved the formation of substantial amounts of undesirable isomeric by-products. Furthermore, most of these previous syntheses of 3-(3-methyl-2-buten-1-yl)-2,4-pentanedione (7a) involved the preparation of expensive intermediates [e.g., $(CH_3)_2C=CHCH_2Cl$ or $(CH_3)_2C=CHCH_2OH$] from isoprene prior to the chemical step used to generate diketone (7a). For two notable exceptions, see references (a) and (e) cited above. However, both of the latter processes afforded unattractive mixtures of products and required costly metallic catalysts.

For previous syntheses of ethyl 2-(3-methyl-2-buten-1-yl)-3-oxobutanoate (7b), see:

(a) H. Pommer, et al., *Justus Liebigs Ann. Chem.* 1969, 729, 52.

(b) European Patent Appl. EP 44,771 (Jan. 27, 1982) [*Chem. Abstracts* 1982, 96, 199115b).

(c) French patent 2,567,511 (Jan. 17, 1986) [*Chem. Abstracts* 1986, 105, 171857a].

(d) A. A. Petrov, et al., *Zh. Obshch. Khim.* 1963, 33, 427 [*Chem. Abstracts* 1963, 59 431c].

(e) U.S. Pat. No. 3,420,827 (Jan. 7, 1969) [*Chem. Abstracts* 1969, 70 67626x].

(f) S. Julia and G. Linstrumelle, *Bull. Soc. Chim. France* 1966, 3490.

(g) Czech. patent 112,243 (Oct. 15, 1964) [*Chem. Abstracts* 1965, 62, 13049e].

(b) Utility of Dicarbonyl Compounds (7)

The dicarbonyl compounds (7) may be used in the synthesis of pseudoionone (2) (systematically named as 6,10-dimethyl-3,5,9-undecatrien-2-one), according to the following reaction sequence:

Reaction Scheme I
(a) (See Summary of the Invention for novel step (a).)
(b)

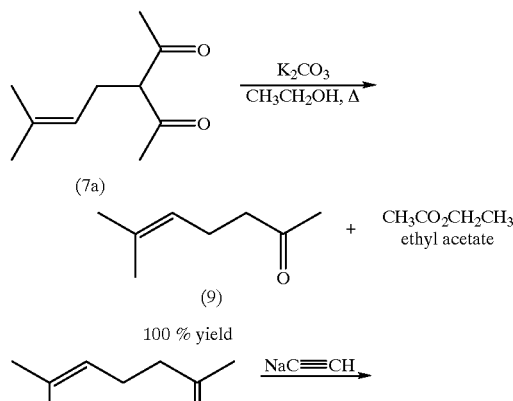

-continued

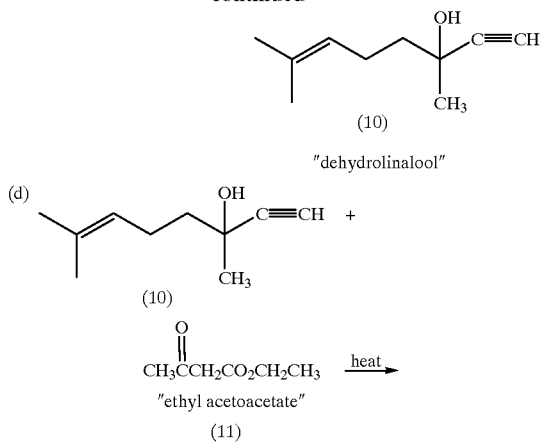

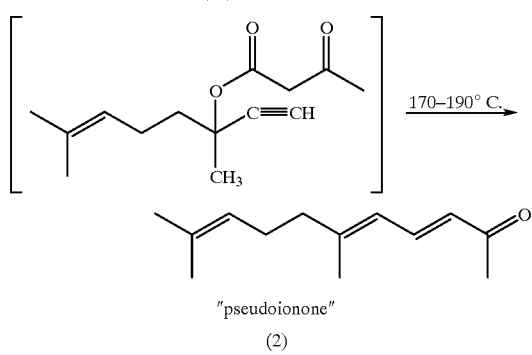

Pseudoionone (2) is a costly specialty chemical that is used in the manufacture of α-ionone (3), used in perfumery, and β-ionone (4), used in perfumery as well as in the manufacture of vitamin A, the anti-acne drugs tretinoin (sold by Ortho Pharmaceutical Corp. under the registered trademark Retin-A) and isotretinoin (sold by Hoffmnan-LaRoche Inc. under the registered trademark Accutane), and several widely used carotenoids, including beta-carotene and canthaxanthin. Pseudoionone can also be used in the manufacture of vitamin E [see: U.S. Pat. No. 5,349,071 (Sep. 20, 1994)] since it is easily converted to isophytol.

One of the earliest routes to pseudoionone involved a crossed-aldol condensation between citral (1) and acetone as shown below:

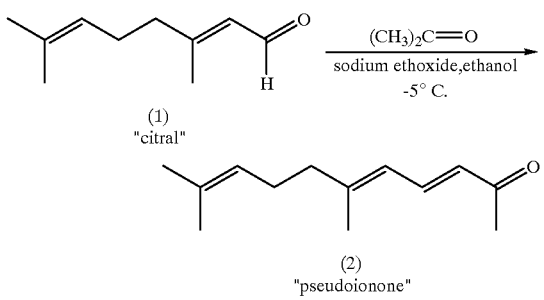

References: *Organic Syntheses,* Collective Volume 3, page 747; H. Hibbert and L. T. Cannon, *J. Am. Chem. Soc.,* 46, 119–130 (1924). The major disadvantage to this route is that it involves use of the costly specialty chemical citral (1), systematically named as 3,7-dimethylocta-2,6-dienal, which is manufactured in a multi-step process generally involving at least five transformations. Once pseudoionone (2) has been obtained, however, it can be converted in high yield and in one step to either α-ionone (3) or β-ionone (4) with little additional cost.

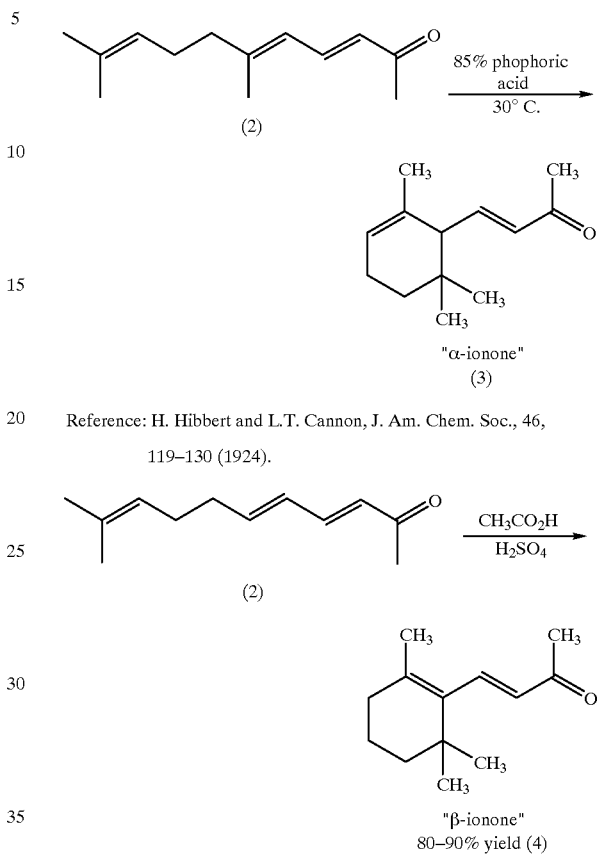

Reference: H. Hibbert and L.T. Cannon, J. Am. Chem. Soc., 46, 119–130 (1924).

Reference: W. Kimel, et al., J. Org. Chem. 23, 153 (1958).

A very attractive alternative route to a structural analogue (18) of pseudoionone that avoids the use of citral has been developed by BASF and is outlined below:

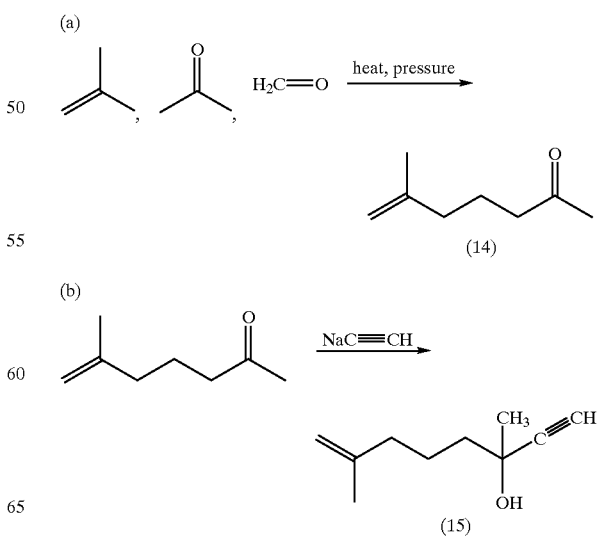

-continued (c)

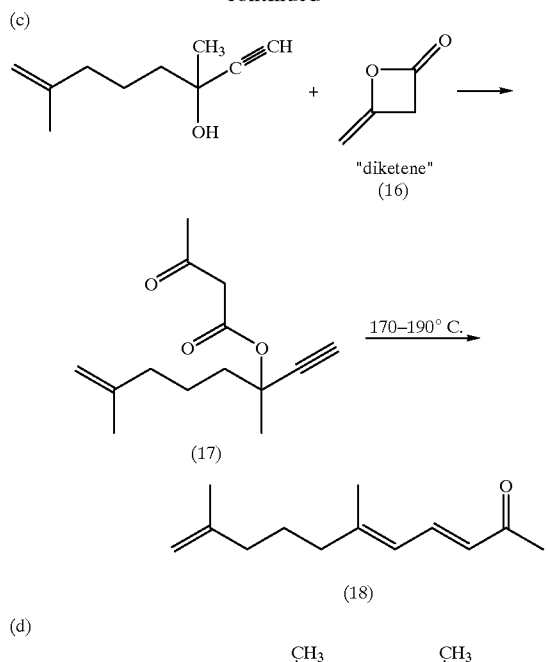

References: W. Reif and H. Grassner, Chemie-Ing.-Techn., 45, 646 (1973) and German patent 1,268,135 (May 16, 1968)--cited in Chem. Abstracts, 69, 86376m (1968).

Although BASF's C-13 polyenone (18) can be converted to β-ionone, polyenone (18) does not possess the correct structure one would need to prepare carotenoids such as lycopene, the red coloring matter of tomatoes. Lycopene has recently been shown to have many useful properties, especially in giving protection against prostate cancer, heart disease, and degenerative eye diseases. Furthermore, the C-8 unsaturated ketone (14) in BASF's route does not possess the proper structure for manufacture of the specialty chemicals linalool (widely used in perfumery) and citral (used extensively in the flavor and fragrance industries). Both of the latter specialty chemicals can be manufactured using known industrial processes starting with the unsaturated ketone (9) obtained in the route of the presently disclosed invention (see section 2(c), below). Likewise, carotenoids such as lycopene are readily prepared from our unsaturated ketone intermediate. An additional advantage of the disclosed process for obtaining C-8 unsaturated ketone (9) from isoprene is that fact that the overall yield is higher and the process is easier to conduct (e.g., atmospheric pressure, room temperature) than the one developed by BASF.

(c) Other Uses of Unsaturated Ketone (9), Produced as an Intermediate in the Synthesis of Pseudoionone Unsaturated ketone (9), shown as a product in step (b) of Scheme I above, may also be used to produce linalool (19) (3,7-dimethyl-1,6-octadien-3-ol, widely used in perfumery) and citral (1) (used extensively in the flavor and fragrance industries), according to the following reaction sequence:

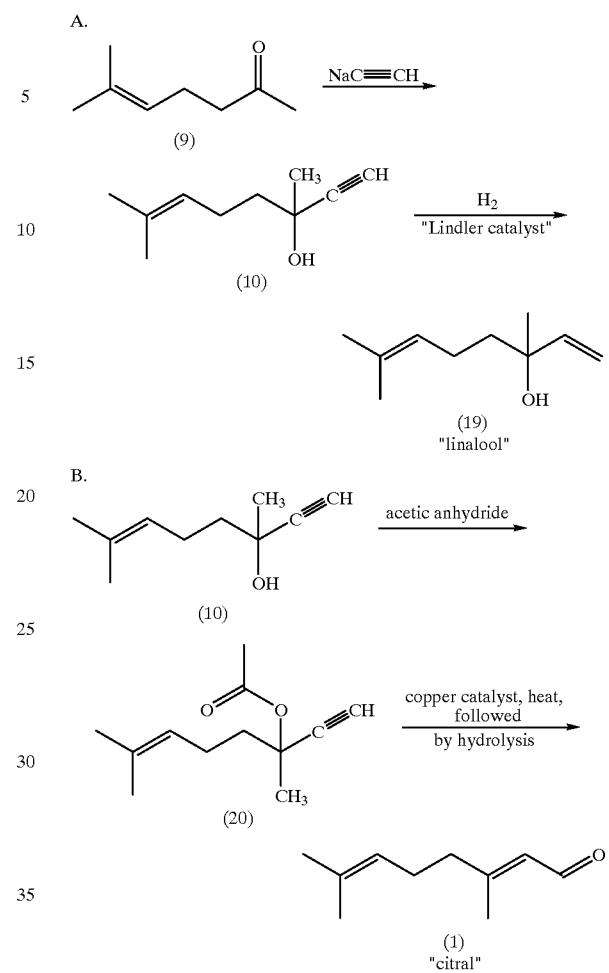

Reference: Czech. patent 126,763 (March 15, 1968)--cited in Chem. Abstracts, 70, 37941d (1969). Subsequent development (e.g., use of a copper catalyst) afforded very high yields of citral.

SUMMARY OF THE INVENTION

The present invention describes a method for preparing dicarbonyl compounds (7), which provides step "(a)" of Reaction Scheme I for the preparation of pseudoionone (2). The method is summarized by the following:

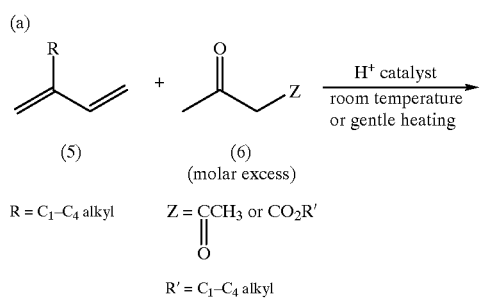

-continued

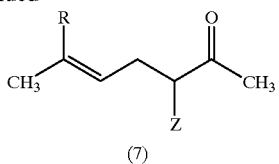

(7)

In one embodiment, R=CH₃ and compound (5) is isoprene,

and compound (6) is 2,4-pentanedione (acetylacetone), and the product (7) is 3-(3-methyl-2-buten-1-yl)-2,4-pentanedione (7a):

(a)

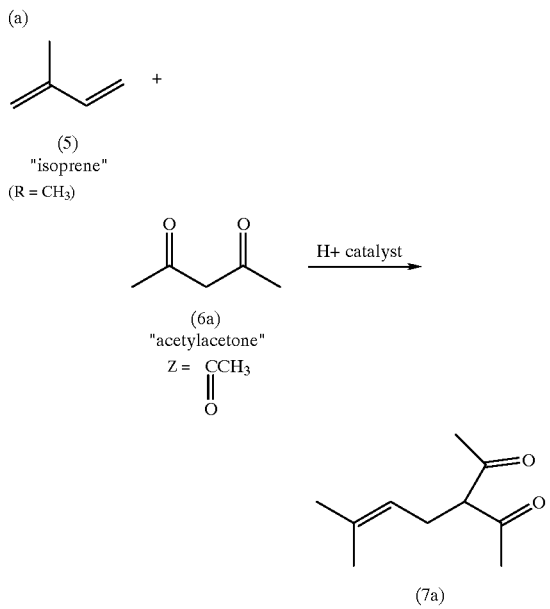

Acetylacetone (6a) is used industrially to remove trace metals during waste water treatments. It also may be used to form various organometallic additives, or as drying agents for varnishes and printer's inks. Acetylacetone (6a) can be prepared by either of the following methods:

A.

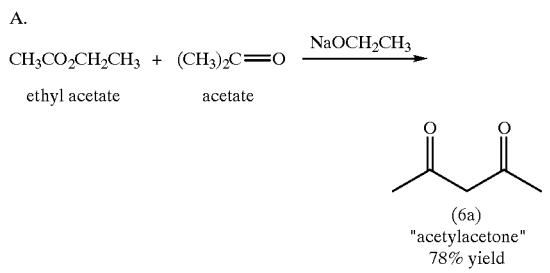

-continued

References: British patent 681,196 (Oct. 22, 1952)--cited in Chem. Abstracts, 48, 710a (1954); K.K. Georgieff, Ind. Eng. Chem., 49, 1067 (1957)--cited in Chem.Abstracts, 52, 9961f (1958); U.S. Pat. No. 2,834,811 (May 13, 1958)--cited in Chem. Abstracts, 52, 19950f (1958).

B.

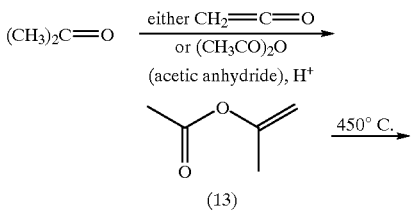

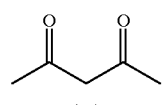

Reference: H. H. Szmant, "Organic Building Blocks of the Chemical Industry," Wiley-Interscience: New York, 1989, p. 317.

In another embodiment, R=CH₃ and compound (5) is isoprene, Z=CO₂R', R'=CH₃CH₂, and compound (6) is ethyl acetoacetate, and the product is ethyl 2-(3-methyl-2-buten-1-yl)-3-oxobutanoate (7b):

(a)

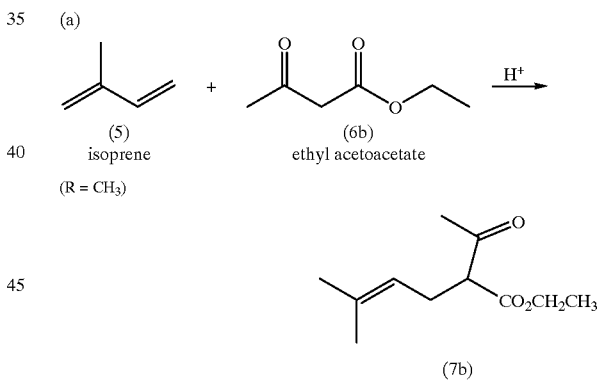

Ethyl 2-(3-methyl-2-buten-1-yl)-3-oxobutanoate (7b) may be converted to compound (9) according to the following reaction:

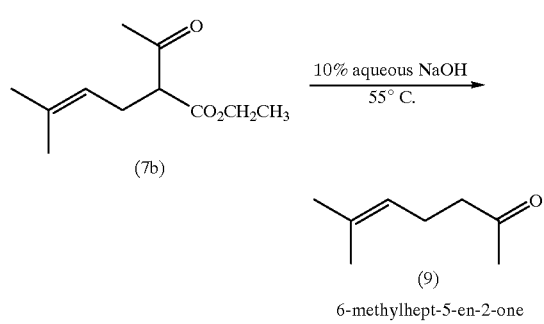

-continued

References for the conversion of (7b) to (9), and related transformations: H. Pommer, et al., Liebigs Ann. Chem. 1969, 729, 52 (conversion of 6 to 4 in that article); U.S. Pat. No. 3,420,827 (Jan. 7, 1969) [Chem. Abstracts 1969, 70, 67626x].

The mechanism of the disclosed process is believed to involve the protonation of isoprene (5) (R=CH$_3$) by a suitable acid catalyst followed by trapping of a thereby generated "prenyl cation" with a 1,3 dicarbonyl reagent (6) that has an appreciable "enol" content to afford dicarbonyl compound (7) in good yield.

The formation of the enol form of compound (6) is illustrated by the following equations:

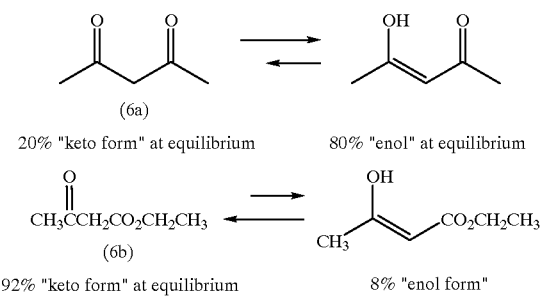

The formation of the prenyl cation is illustrated by the following reaction:

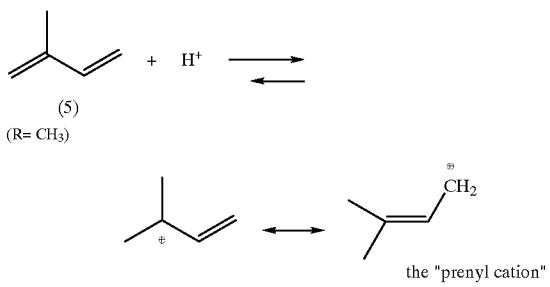

The "prenyl cation," formed by the addition of a proton to isoprene, is trapped by the "enol form" of reactant (6) (see keto-enol equilibrium reactions, above) to give the desired product (7). If the prenyl cation reacts with isoprene, "polymeric" terpene products (i.e., C-10, C-15, etc.) are obtained.

The novel process requires the following reagents and reaction conditions:

(a) a conjugated alkadiene of general structure (5). Isoprene (R=CH$_3$) is the preferred diene.

(b) a 1,3-dicarbonyl compound possessing a significant "enol" content. Such a reactant must be used in molar excess and serves as the solvent. No other solvent is required. Suitable dicarbonyl compounds (6) include acetylacetone (2,4-pentanedione) (6a) and ethyl acetoacetate (6b). Since the latter compound exhibits a smaller enol content than does acetylacetone, it is not as effective at trapping the "prenyl cation," and the process proceeds more slowly in ethyl acetoacetate than in acetylacetone. Furthermore, use of ethyl acetoacetate as the solvent for this process requires the absence of significant amounts of water since its ester functionality is subject to hydrolysis. Hence, acetylacetone is the preferred solvent/reactant. If one uses ethyl acetoacetate as a reactant, polyphosphoric acid is a preferred catalyst.

(c) The process requires an acid catalyst selected from one of the following categories:

(i) an inorganic acid possessing a $K_a$ (relative to water) that is greater than $10^{-3}$. Phosphoric acid (85–100%) and polyphosphoric acid are preferred catalysts. Aqueous sulfuric acid (H$_2$SO$_4$) can also be used to catalyze this process, although it is not a preferred catalyst.

(ii) an organic acid possessing a $K_a$ (relative to water) that is greater than $10^{-1}$. Sulfonic acids (RSO$_3$H) are useful catalysts for this process—e.g., p-toluenesulfonic acid monohydrate (Example VI).

(iii) The acid catalyst does not have to be soluble in the reaction mixture. For example, strongly acidic resins can be used to catalyze the process (Example VII).

(iv) Hydrochloric acid (HCl), although it is a strong acid, cannot be used to catalyze this process (Example V). Although the "prenyl cation" is generated when HCl protonates isoprene, the chloride anion traps the intermediate—thereby generating (CH$_3$)$_2$C=CHCH$_2$Cl, not the desired product (7).

(d) Dropwise addition of isoprene over a period of several hours to the dicarbonyl compound (containing an acid catalyst) is required for a good yield (see discussion of formation of prenyl cation, above).

(e) The reaction occurs at room temperature if one uses a strong acid catalyst such as p-toluenesulfonic acid or even the more weakly acidic polyphosphoric acid. If phosphoric acid is used in the presence of H$_2$O (e.g., 85% H$_3$PO$_4$), the reaction is slower and requires gentle heating (60–90° C.). Temperatures that exceed 140° C. (i.e., the boiling point of acetylacetone) are not useful in this process—i.e., too many side-reactions occur.

Advantages of the disclosed process include the following:

(a) No costly raw materials are utilized.

(b) The process avoids the use of organic halides.

(c) Mixtures of isomeric products are not a serious problem in the conversion of isoprene to dicarbonyl compound (7). The latter product is easy to purify since (7a) is soluble in dilute aqueous NaOH (in contrast to the by-products).

(d) The disclosed process generates a product (7), and subsequently (9) that possesses the correct structure for the preparation of valuable specialty chemicals such as linalool, citral, pseudoionone, and lycopene. BASF's route to "methyl-heptenone" generates an isomeric compound (14) that can only be used to prepare α- or β-ionone.

The disclosed reaction is surprisingly useful in producing dicarbonyl compound (7) in high yield. The results are unexpected and nonobvious for a number of reasons:

(a) J. A. Miller and coworkers have reported [J. Chem. Soc. Perkin I 1972, 692] that diketone (7a) readily cyclizes, even under mildly acidic conditions, to give 5-acetyl-3,4-dihydro-2,2,6-trimethyl-2H-pyran (8) in high yield, according to the following reaction:

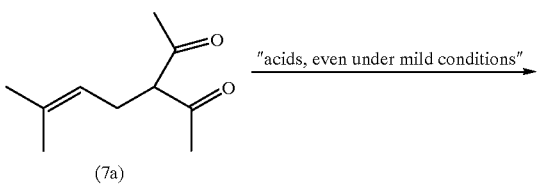

-continued

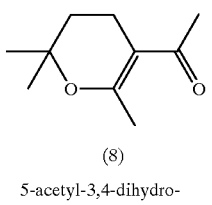

(8)

5-acetyl-3,4-dihydro-
2,2,6-trimethyl-2H-pyran

This prior art teaches away from attempting to prepare compound (7) under acidic conditions. Miller et al. reported an 84% yield of (8) after a reaction time of 90 minutes at 0° C. The disclosed process surprisingly produces very little, if any, of this heterocyclic compound (8) even after prolonged reaction times.

(b) The conversion of (5) to (7) is acid-catalyzed. However, carboxylic acids such as oxalic acid dihydrate ($K_a$=5.4×10$^{-2}$) and dichloroacetic acid ($K_a$=5.5×10$^{-2}$) that are stronger than phosphoric acid ($K_a$=7.1×10$^{-3}$) failed to catalyze the process even at 80° C.—i.e., no reaction occurred! (References for these acidity values: "The Merck Index," Ninth Edition, page 956; *Organic Chemistry*, Third Edition, page 600, by Morrison and Boyd.)

DETAILED DESCRIPTION OF THE INVENTION

The following examples are presented for purposes of illustration and should not be construed as limiting the invention which is delineated in the claims.

EXAMPLE I

Preparation of 3-(3-Methyl-2-buten-1-yl)-2,4-pentanedione by Treatment of Isoprene with 2,4-Pentanedione Containing Polyphosphoric Acid as a Catalyst Polyphosphoric acid (600 mg), 2,4-pentanedione (5.0 mL), and isoprene (0.25 mL, 2.5 mmoles), all of which were purchased from Aldrich Chemical Co., Milwaukee, Wis., were added to a 10 mL, 1-neck reaction flask fitted with a lightly-greased glass stopper [to minimize loss of the volatile isoprene (bp 34° C.)]. This mixture was subsequently stirred at room temperature for 24 hours. The product was isolated by dilution of the reaction mixture with 40 mL of 15% (w/v) aqueous sodium chloride and extraction with 30 mL of hexane. [NOTE: If one intends to recycle unreacted 2,4-pentanedione, a fractional distillation of the organic layer can be done at this point.] After subsequent washing of the organic layer with 3% (w/v) aqueous sodium chloride (10×50 mL, to ensure removal of 2,4-pentanedione) and saturated aqueous sodium chloride (1×25 mL), it was dried over anhydrous magnesium sulfate and filtered. Removal of the hexane by evaporation at reduced pressure and subsequent evaporative distillation afforded 247 mg (59% yield) of the named diketone: boiling point 89°–98° C. (bath temperature, 0.35 mm). The identity of this compound was ascertained by IR and proton NMR analysis (recorded at 400 MHz). The latter spectrum exhibited a broad triplet at δ 4.98 (CH=C), a triplet (J=7.2 Hz) at δ 3.65 (H bonded to C-3), a doublet (J=6.4 Hz) at δ 2.91 (CH$_2$ bonded to C-3 in the "enol form" of the named diketone), and a triplet (J=6.8 Hz) at δ 2.53 (CH$_2$ bonded to C-3 in the "keto form" of the named diketone). Approximately 20% of the distilled product consisted of a mixture of unidentified by-products (presumably C-10 and/or C-15 hydrocarbons obtained by reaction of the initially generated "prenyl-cation" with isoprene instead of the enol form of 2,4-pentanedione). The latter by-products were readily separated from the named diketone by dissolving the distillate in 20 mL of hexane and washing the organic layer with 1 M aqueous sodium hydroxide (3×15 mL)—from which aqueous washes the named diketone can be recovered by subsequent acidification and extraction with ether. The proton NMR spectrum of this unidentified mixture of by-products (wt.: approximately 50 mg) exhibited a singlet at δ 1.26 [C(CH$_3$)$_2$] but lacked any signals in the region of δ 2.0–2.1—an indication that 5-acetyl-3,4-dihydro-2,2,6-trimethyl-2H-pyran was not one of the by-products. The proton NMR spectrum of the latter heterocyclic compound is known to exhibit a singlet at δ 2.05. See: J. A. Miller, et al., *J. Chem. Soc. Perkin I*, 692 (1972).

If one desires to maximize the yield of the named diketone, the controlled addition of isoprene (perhaps dissolved in a small amount of 2,4-pentanedione) over a period of several hours to a mixture of polyphosphoric acid and excess 2,4-pentanedione at 40°–50° C. is recommended. The reaction mixture would have to be maintained under sufficient pressure to ensure that isoprene (bp 34° C.) remains in the liquid phase.

EXAMPLE II

Preparation of Ethyl 2-(3-Methyl-2-buten-1-yl)-3-oxobutanoate by Treatment of Isoprene with Ethyl Acetoacetate Containing Polyphosphoric Acid as a Catalyst Polyphosphoric acid (530 mg), ethyl acetoacetate (6.0 mL), and isoprene (0.25 mL, 2.5 mmoles), all of which were purchased from Aldrich Chemical Co., Milwaukee, Wis., were added to a 10-mL, 1-neck reaction flask fitted with a glass stopper (to minimize loss of the volatile isoprene). This mixture was subsequently stirred at room temperature for 19 hours. The product was isolated by dilution of the reaction mixture with 60 mL of 15% (w/v) aqueous sodium chloride and extraction with 40 mL of hexane. After subsequent washing of the organic layer with 2:1 (v/v) water:methyl alcohol (7×50 mL, to ensure removal of ethyl acetoacetate) and saturated aqueous sodium chloride (1×25 mL), it was dried over anhydrous magnesium sulfate and filtered. Removal of the hexane by evaporation at reduced pressure and subsequent evaporative distillation afforded 134 mg (27% yield) of the named keto ester: boiling point 90°–102° C. (bath temperature, 0.35 mm). The identity of this product was ascertained by IR (v$_{max}$ 1740, 1715 cm$^{-1}$) and proton NMR analysis (recorded at 400 MHz). The latter spectrum exhibited a broad triplet at δ 5.02 (CH=C), a triplet (J=7.6 Hz) at δ 3.43 (H bonded to C-2), a singlet at δ 2.22 (CH$_3$C=O), and a broad triplet (J=7 Hz) at δ 2.54 (CH$_2$ bonded to C-2 of the named keto ester). The distillate also contained a minor amount of unidentified by-products similar to those obtained in Example I (presumably C-10 and/or C-15 hydrocarbons obtained by reaction of the initially generated "prenyl cation" with isoprene instead of the enol form of ethyl acetoacetate.

If one desires to maximize the yield of the named keto ester, the controlled addition of isoprene (perhaps dissolved in a small amount of ethyl acetoacetate) over a period of several hours to a mixture of polyphosphoric acid and excess ethyl acetoacetate at 50°–60° C. and several atmospheres pressure is recommended.

EXAMPLE III

Preparation of 3-(3-Methyl-2-buten-1-yl)-2,4-pentanedione by Treatment of Isoprene with 2,4-Pentanedione Containing Aqueous Phosphoric Acid as a Catalyst 2,4-Pentanedione (12.0 mL), isoprene (0.25 mL, 2.5 mmoles), and 85% phosphoric acid (1.00 mL) were added to a 35 mL pressure vessel (heavy glass wall, catalog #CG-1880-02, purchased from Chemglass, Vineland, N.J.). After adding a small spin bar and sweeping the system briefly with nitrogen, the vessel was closed; and the mixture was heated, with continuous stirring, at 80° C. (external oil bath temperature) for 14 hours. After cooling the mixture to room temperature, the product was isolated by dilution of the reaction mixture with 100 mL of 15% (w/v) aqueous sodium chloride and extraction with 50 mL of hexane. After subsequent washing of the organic layer with 3% (w/v) aqueous sodium chloride (10×100 mL, to ensure removal of 2,4-pentanedione) and saturated aqueous sodium chloride (1×50 mL), it was dried over anhydrous magnesium sulfate and filtered. Removal of the hexane by evaporation at reduced pressure and subsequent evaporative distillation afforded 135 mg (32% yield) of the named diketone: boiling point 82°–90° C. (bath temperature, 0.35 mm). The spectral properties of this material were virtually identical to those exhibited by the product prepared in accordance with the procedure of Example I.

EXAMPLE IV

Attempt To Prepare 3-(3-Methyl-2-buten-1-yl)-2,4-pentanedione by Treatment of Isoprene with 2,4-Pentanedione Containing Dichloroacetic Acid as a Catalyst 0.50 mL (6.1 mmoles) of dichloroacetic acid (purified-grade, purchased from Fisher Scientific Co.), 6.0 mL of 2,4-pentanedione, and 0.25 mL (2.5 mmoles) of isoprene were added to a 15-mL, 1-neck reaction flask fitted with a double-jacketed, coiled reflux condenser connected to an apparatus similar to that described by Johnson and Schneider [*Org. Synth.*, 30, 18 (1950)] so that the mixture in the flask could be protected from atmospheric moisture throughout the course of the reaction. This mixture was subsequently heated, with continuous stirring, at 80° C. (external oil bath temperature) for 25 hours, after which it was cooled to room temperature. [NOTE: The odor of unreacted isoprene was detected prior to diluting the reaction mixture with aqueous sodium chloride.] Isolation of the product as described in the procedure of Example I afforded only 21 mg of crude material, the proton NMR spectrum of which detected only a trace amount of the named diketone. Hence the conversion of isoprene to the desired product was less than 2%.

Treatment of 0.25 mL of isoprene in 6.0 mL of 2,4-pentanedione containing 0.50 mL (7.35 mmoles) of 85% phosphoric acid in an identical reaction apparatus at 80° C. for 21 hours afforded 191 mg (45% yield) of crude material, proton NMR analysis of which indicated that the major component was the desired named diketone. Hence the conversion of isoprene to diketone exceeded 20%.

EXAMPLE V

Use of Concentrated Aqueous Hydrochloric Acid as a Catalyst 2,4-Pentanedione (12.0 mL), concentrated aqueous hydrochloric acid (1.0 mL, 12.4 mmoles), and isoprene (0.25 mL, 2.5 mmoles) were added to a 25-mL, 1-neck reaction flask fitted with a glass stopper (to minimize loss of the volatile isoprene). This mixture was subsequently stirred at room temperature for 18 hours. Isolation of the product as described in the procedure of Example III afforded 161 mg of crude material, the proton NMR spectrum of which indicated the presence of little (if any) of the desired product: 3-(3-methyl-2-buten-1-yl)-2,4-pentanedione. Instead, the major product was shown to be 1-chloro-3-methyl-2-butene, the IR and proton NMR spectral properties of which were identical to those exhibited by an authentic sample of the latter compound (purchased from Aldrich Chemical Co., Milwaukee, Wis.). Although isoprene was protonated by HCl under these reaction conditions, the thereby-generated "prenyl cation" was trapped by chloride anion and not by the "enol form" of 2,4-pentanedione.

EXAMPLE VI

Preparation of 3-(3-Methyl-2-buten-1-yl)-2,4-pentanedione by Treatment of Isoprene with 2,4-Pentanedione Containing p-Toluenesulfonic Acid as a Catalyst 2,4-Pentanedione (6.0 mL), p-toluenesulfonic acid monohydrate (1.1 g, 5.8 mmoles, purchased from Fisher Scientific Co.), and isoprene (0.25 mL, 2.5 mmoles) were added to a 10-mL, 1-neck reaction flask fitted with a glass stopper [to minimize loss of the volatile isoprene]. This mixture was subsequently stirred at room temperature for 20 hours. Isolation of the product as described in the procedure of Example I afforded 162 mg (39% yield) of the named diketone, the spectral properties of which were identical to those exhibited by the product prepared in accordance with the procedure of Example I. As in the latter experiment, approximately 20% of the product consisted of a mixture of unidentified by-products, presumably obtained by reaction of the initially generated "prenyl cation" with isoprene instead of the enol form of 2,4-pentanedione. Slow addition of isoprene to the reaction mixture is advisable to maximize the yield of the named diketone.

EXAMPLE VII

Preparation of 3-(3-Methyl-2-buten-1-yl)-2,4-pentanedione by Treatment of Isoprene with 2,4-Pentanedione in the Presence of a Strongly Acidic Ion-Exchange Resin 2,4-Pentanedione (10 mL), 1.02 g (weight of resin after drying it in an oven at 140° C. for 2 hours to remove surface water) of Dowex® 50X8-400 ion-exchange resin, purchased from Aldrich Chemical Co., catalog #21,751-4), and isoprene (0.25 mL, 2.5 mmoles) were added to a 15-mL, 1-neck reaction flask fitted with a double-jacketed, coiled reflux condenser connected to an apparatus similar to that described by Johnson and Schneider [*Org. Synth.*, 30, 18 (1950)] so that the mixture in the flask could be protected from atmospheric moisture throughout the course of the reaction. This mixture was subsequently heated, with continuous stirring, at 45° C. (external oil bath temperature) for 22 hours, after which it was cooled to room temperature. After removal of the resin by filtration through a plug of glass wool, isolation of the product as described in the procedure of Example III afforded 155 mg (37% yield) of the named diketone accompanied by the usual mixture of unidentified by-products obtained when the initially generated "prenyl cation" reacts with isoprene instead of with 2,4-pentanedione.

EXAMPLE VIII

Preparation of 3-(3-Methyl-2-buten-1-yl)-2,4-pentanedione by Slow Addition of Isoprene to 2,4-Pentanedione Containing Polyphosphoric Acid as a Catalyst Polyphosphoric acid (580 mg) and 2,4-pentanedione (6.0 mL) were added to a 15-mL, 1-neck reaction flask containing a magnetic stirring bar and fitted with a septum cap (to allow addition of isoprene to be made using a syringe). This mixture was stirred at room temperature for 30 minutes, after which reaction was initiated by addition of 300 microliters (μL) of a 4:1 (v/v) mixture of 2,4-pentanedione:isoprene. Every 3 hours, an additional portion (300 μL) of 4:1 (v/v) 2,4-pentanedione:isoprene was added to the stirred reaction mixture until 4 such portions [4×300 μL; the equivalent of 4×60 μL (2.4 mmoles) of isoprene] had been added over 9 hours. The mixture was subsequently stirred at room temperature for an additional 20 hours. The product was isolated by dilution of the reaction mixture with 60 mL of 15% (w/v) aqueous sodium chloride and extraction with hexane. After subsequent washing of the organic layer with 15% (w/v) aqueous sodium chloride (9×50 mL, to ensure removal of most of the 2,4-pentanedione), it was dried over anhydrous magnesium sulfate and filtered. [NOTE: If one washes the organic layer thoroughly with 3% (w/v) aqueous sodium chloride, all residual 2,4-pentanedione is removed from the product; however, small amounts (approximately 3–5%) of the named ketone (i.e., the desired product) are removed during each wash. Hence a significant amount (perhaps 30–40%) of the desired product was lost during the isolation procedure used in Examples I, III, IV, VI, and VII.] Removal of the hexane by evaporation at reduced pressure afforded 462 mg of material shown by proton NMR analysis to contain (approximately 35% of the mixture) some residual 2,4-pentanedione. The latter was removed by evaporative distillation at 40–65° C. (bath temperature, 2.0 mm)—during which process a minor amount of the desired product was probably lost via co-distillation. Subsequent distillation afforded 245 mg (61% yield) of the named diketone: boiling point 80–90° C. (bath temperature, 0.20 mm).

The spectral properties of this product were consistent with those exhibited by the product prepared in accordance with the procedure of Example I. More significantly, proton NMR analysis indicated that the unidentified by-products obtained in Example I comprised less than 10% of the distilled product. Hence, controlled addition of isoprene to the reaction mixture improves the process.

What is claimed is:

1. A method for preparing a dicarbonyl compound of the formula

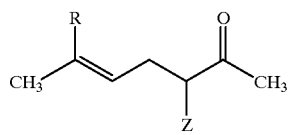

reacting a conjugated alkadiene compound of the formula

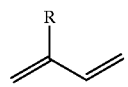

with a 1,3-dicarbonyl compound of the formula

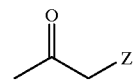

(wherein R and Z are defined above)
in the presence of an acid catalyst.

2. The method of claim 1 wherein the acid catalyst comprises an inorganic acid having a $K_a$ (relative to water) that is greater than $10^{-3}$.

3. The method of claim 2 wherein the acid catalyst comprises phosphoric acid.

4. The method of claim 3 wherein the phosphoric acid has a concentration of between about 85% and 100%.

5. The method of claim 2 wherein the acid catalyst comprises polyphosphoric acid.

6. The method of claim 2 wherein the acid catalyst comprises aqueous sulfuric acid.

7. The method of claim 1 wherein the acid catalyst comprises an organic acid having a $K_a$ (relative to water) that is greater than $10^{-1}$.

8. The method of claim 7 wherein the acid catalyst comprises a sulfonic acid.

9. The method of claim 8 wherein the sulfonic acid comprises p-toluenesulfonic acid.

10. The method of claim 7 wherein the acid catalyst comprises a strongly acidic resin.

11. The method of claim 1 wherein R=CH$_3$.

12. The method of claim 1 wherein

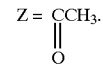

13. The method of claim 1 wherein

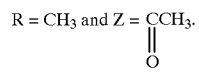

14. The method of claim 1 wherein Z=CO$_2$CH$_2$CH$_3$.

15. The method of claim 1 wherein the conjugated alkadiene compound is added slowly to a reaction mixture comprising the 1,3-dicarbonyl compound and the acid catalyst.

16. A method of preparing 3-(3-methyl-2-buten-1-yl)-2,4-pentanedione comprising:

providing a reaction mixture comprising acetylacetone and an acid catalyst; and slowly adding isoprene to the reaction mixture.

17. The method of claim 16 wherein the acid catalyst comprises polyphosphoric acid.

18. The method of claim 17 wherein the reaction mixture is maintained at a temperature of about 20° C.

19. The method of claim 16 wherein the acid catalyst comprises phosphoric acid.

20. The method of claim 19 wherein the phosphoric acid has a concentration of about 85%.

21. The method of claim 20 wherein the reaction mixture is maintained at a temperature of about 80° C.

* * * * *

UNITED STATES PATENT AND TRADEMARK OFFICE
CERTIFICATE OF CORRECTION

PATENT NO. : 6,049,010
DATED : April 11, 2000
INVENTOR(S) : Babler et al.

It is certified that error appears in the above-identified patent and that said Letters Patent is hereby corrected as shown below:

Claim 1
Col. 15, line 55

Below the first structure, insert --wherein $R = C_1\text{-}C_4$ alkyl $$Z = CO_2R' \text{ or } \underset{O}{\overset{\parallel}{C}}CH_3$$

and $R' = C_1\text{-}C_4$ alkyl, comprising: --

Signed and Sealed this

Sixth Day of March, 2001

Attest:

NICHOLAS P. GODICI

Attesting Officer     Acting Director of the United States Patent and Trademark Office